US011534097B2

(12) United States Patent
Wang et al.

(10) Patent No.: US 11,534,097 B2
(45) Date of Patent: Dec. 27, 2022

(54) DETECTION OF ELECTROCARDIOGRAPHIC SIGNAL

(71) Applicant: ANHUI HUAMI INFORMATION TECHNOLOGY CO., LTD., Anhui (CN)

(72) Inventors: Kongqiao Wang, Anhui (CN); Wei Zhao, Anhui (CN); Yazhao Li, Anhui (CN); Xiao Li, Anhui (CN)

(73) Assignee: Anhui Huami Information Technology Co., Ltd., Anhui (CN)

( * ) Notice: Subject to any disclaimer, the term of this patent is extended or adjusted under 35 U.S.C. 154(b) by 386 days.

(21) Appl. No.: 16/750,568

(22) Filed: Jan. 23, 2020

(65) Prior Publication Data
US 2020/0155024 A1 May 21, 2020

Related U.S. Application Data

(63) Continuation of application No. PCT/CN2018/097917, filed on Aug. 1, 2018.

(30) Foreign Application Priority Data
Aug. 3, 2017 (CN) .......................... 201710656849.8

(51) Int. Cl.
*A61B 5/352* (2021.01)
*A61B 5/316* (2021.01)
(Continued)

(52) U.S. Cl.
CPC .............. *A61B 5/316* (2021.01); *A61B 5/352* (2021.01); *G06N 3/0454* (2013.01); *G06N 3/08* (2013.01)

(58) Field of Classification Search
CPC ...... A61B 5/316; A61B 5/352; G06N 3/0454; G06N 3/08
See application file for complete search history.

(56) References Cited

U.S. PATENT DOCUMENTS 10,779,744 B2 * 9/2020 Rapin .................... A61B 5/361
2004/0230105 A1 * 11/2004 Geva .................... A61B 5/7264
600/509

(Continued)

FOREIGN PATENT DOCUMENTS

CN          102779234 A       11/2012
CN          102781140 A       11/2012

(Continued)

OTHER PUBLICATIONS

Japanese Office Action, dated Sep. 14, 2021 by the Japan Patent Office, in Japanese Patent Application No. 2020-526667, 8 pp.

(Continued)

*Primary Examiner* — Ankit D Tejani
*Assistant Examiner* — Joshua Brendon Solomon
(74) *Attorney, Agent, or Firm* — Greenblum & Bernstein, P.L.C.

(57) ABSTRACT

The present application provides a method and apparatus for detecting an ECG signal and an electronic device. According to an example of the method, an ECG signal with a set time length is segmented to obtain a first set number of single heartbeats; feature data corresponding to each of the first set number of single heartbeats is determined to obtain a first set number of feature data; and a pathological category of the ECG signal with the set time length is determined based on the ECG signal with the set time length and the first set number of feature data.

15 Claims, 11 Drawing Sheets

(51) Int. Cl.
*G06N 3/04* (2006.01)
*G06N 3/08* (2006.01)

(56) References Cited

U.S. PATENT DOCUMENTS

| | | | |
|---|---|---|---|
| 2008/0285819 | A1 | 11/2008 | Konofagou et al. |
| 2009/0171221 | A1 | 7/2009 | Liao et al. |
| 2013/0066211 | A1 | 3/2013 | Konofagou et al. |
| 2017/0206450 | A1 | 7/2017 | Umeda |
| 2018/0032689 | A1* | 2/2018 | Kiranyaz ............... G16H 50/20 |
| 2020/0155024 | A1 | 5/2020 | Wang |

FOREIGN PATENT DOCUMENTS

| | | | |
|---|---|---|---|
| CN | 104783782 | A | 7/2015 |
| CN | 106344004 | A | 1/2017 |
| CN | 106779051 | A | 5/2017 |
| CN | 106934799 | A | 7/2017 |
| CN | 107516075 | A | 12/2017 |
| EP | 3644220 | A1 | 4/2020 |
| JP | 2017129896 | A | 7/2017 |
| KR | 20140063100 | A | 5/2014 |
| KR | 20160075677 | A | 6/2016 |
| WO | 2017075856 | A1 | 5/2017 |
| WO | 2017091736 | A1 | 6/2017 |
| WO | 2019024861 | A1 | 2/2019 |

OTHER PUBLICATIONS

Japanese Patent Office, Office Action issued in Application No. 2020-526667, dated Feb. 24, 2021, 13 pages. (Submitted with English Language Machine Translation).
State Intellectual Property Office of the People's Republic of China, Third Office Action and Search Report Issued in Application No. 201710656849.8, dated Mar. 3, 2020, 21 pages (Submitted with Machine Translation).
ISA State Intellectual Property Office of the People's Republic of China, Written Opinion of the International Searching Authority Issued in Application No. PCT/CN2018/097917, dated Nov. 6, 2018, WIPO, 5 pages.
ISA State Intellectual Property Office of the People's Republic of China, International Search Report Issued in Application No. PCT/CN2018/097917, dated Nov. 6, 2018, WIPO, 4 pages.
State Intellectual Property Office of the People's Republic of China, Office Action and Search Report Issued in Application No. 2017106568498, dated Dec. 26, 2018, 7 pages,(Submitted with Machine Translation).
State Intellectual Property Office of the People's Republic of China, Office Action and Search Report Issued in Application No. 2017106568498, dated Aug. 16, 2019, 10 pages,(Submitted with Machine Translation).
Karpagachelvi S, et al; ECG feature extraction techniques-a survey approach.; (IJCSIS) International Journal of Computer Science and Information Security; vol. 8, No. 1, Apr. 2010.
Huanhuan M, et al; Classification of electrocardiogram signals with deep belief networks; Computational Science and Engineering (CSE), 2014 IEEE 17th International Conference on. IEEE, 2014: 7-12.
Kiranyaz S, et al; Real-Time Patient-Specific ECG Classification by 1-D Convolutional Neural Networks.; IEEE Transactions on Biomedical Engineering, vol. 00, No. 00, 2015/.
Jin L, et al; Ensemble Deep Learning for Biomedical Time Series Classification; Computational Intelligence and Neuroscience, vol. 2016.
Indian Intellectual Property Office, Office Action Issued in Application No. 202047007980, dated Jul. 30, 2021, 6 pages.
European Patent Office, Office Action Issued in Application No. 18841762.0, dated Jun. 22, 2021, Netherlands, 8 pages.
Yi Zheng et al.: "Time Series Classification Using Multi-Channels Deep Convolutional Neural Networks", In: "ICIAP International Conference on Image Analysis and Processing, 17th International Conference, Naples, Italy, Sep. 9-13, 2013. Proceedings", Jan. 1, 2014 (Jan. 1, 2014), Springer, Berlin, Heidelberg, 13 pages.
Daiana Petry et al.: "System to ECG Signals Variability Analysis: Heart Rate Variability and QT Interval Variability", In: "Imaging the future medicine : World Congress on Medical Physics and Biomedical Engineering 2006, Aug. 27-Sep. 1, 2006, COEX Seoul, Korea", Jan. 1, 2007 (Jan. 1, 2007), Springer, DE, 5 pages.
Canadian Intellectual Property Office, Canada Office Action Issued in Canadian Patent Application No. 3,071,699 dated Mar. 25, 2021 (4 pages).
Canada Patent Office, Office Action Issued in Application No. 3071699, dated Dec. 23, 2021, 5 pages.
Korean Intellectual Property Office, Office Action Issued in Application No. 10-2020-7005872, dated Feb. 28, 2022, 15 pages. (Submitted with English Language Machine Translation).
Partial Supplemental European Search Report, dated Jun. 24, 2020 by the European Patent Office (EPO), in Application No. 18841762.0, Germany.
Quazi Abidur Rahman et al., "Utilizing ECG-Based Heartbeat Classification for Hypertrophic Cardiomyopathy Identification", IEEE Transaction on Nanobioscience, IEEE Service Center, Piscataway, NY, vol. 14, No. 5, Jul. 1, 2015, pp. 505-512.
U. Rajendra Acharya et al., "Application of deep convolution neural network for automated detection of myocardial infarction using ECG signals", Information Sciences, Amsterdam, NL, vol. 415, Jun. 23, 2017, pp. 190-198.
Extended European Search Report, dated Oct. 7, 2020 by the European Patent Office (EPO), in Application No. 18841762.0, 14 pages.
Linpeng Jin et al., "Classification of normal and abnormal ECG records using lead convolutional neural network and rule inference", Science China, Informational Sciences, vol. 60, 078103:1-078103:3, doi: 10.1007/s11432-016-9047-6, May 19, 2017, 3 pages.

* cited by examiner

DETECTION OF ELECTROCARDIOGRAPHIC SIGNAL

CLAIM FOR PRIORITY

This application is a Continuation of PCT/CN2018/097917 filed Aug. 1, 2018, and claims the priority benefit of Chinese application 201710656849.8 filed Aug. 3, 2017, the contents of which are expressly incorporated by reference herein in their entireties.

TECHNICAL FIELD

The present application relates to the field of electronic technology, and in particular, to a method and apparatus for detecting an electrocardiographic (ECG) signal and an electronic device.

BACKGROUND

In recent years, with the rise of deep learning methods, researchers have increasingly begun to adopt the pattern of training neural networks for electrocardiographic (ECG) signal classification and identification. However, in most cases, single heartbeats of an ECG signal are identified and classified, and pathological identification of continuous ECG multiple heartbeats has not yet been performed.

SUMMARY

In view of this, the present application provides a new technical solution that can perform pathological diagnosis on a continuous ECG signal.

In order to achieve the above objective, the present application provides the following technical solutions.

According to a first aspect of the present application, there is provided a method of detecting an ECG signal, comprising:

segmenting an ECG signal with a set time length to obtain a first set number of single heartbeats;

determining feature data corresponding to each of the first set number of single heartbeats to obtain a first set number of feature data; and determining a pathological category of the ECG signal with the set time length based on the ECG signal with the set time length and the first set number of feature data.

According to a second aspect of the present application, there is provided a method of detecting an ECG signal, comprising:

determining a pathological category of an ECG signal with a set time length through a second convolutional neural network;

if the pathological category indicates that the ECG signal is abnormal, segmenting the ECG signal with the set time length to obtain a first set number of single heartbeats; and inputting data of the first set number of single heartbeats to a first convolutional neural network to determine locations of one or more abnormal heartbeats in the first set number of single heartbeats through the first convolutional neural network.

According to a third aspect of the present application, there is provided an apparatus for detecting an ECG signal, comprising:

a first segmenting module configured to segment an ECG signal with a set time length to obtain a first set number of single heartbeats;

a first determining module configured to determine feature data corresponding to each of the first set number of single heartbeats obtained by the first segmenting module to obtain a first set number of feature data; and a second determining module configured to determine a pathological category of the ECG signal with the set time length based on the ECG signal with the set time length and the first set number of feature data determined by the first determining module.

According to a fourth aspect of the present application, there is provided an apparatus for detecting an ECG signal, comprising:

a fourth determining module configured to determine a pathological category of an ECG signal with a set time length through a second convolutional neural network;

a second segmenting module configured to, if the pathological category determined by the fourth determining module indicates that the ECG signal is abnormal, segment the ECG signal with the set time length to obtain a first set number of single heartbeats; and a fifth determining module configured to input data of the first set number of single heartbeats obtained by the second segmenting module to a first convolutional neural network to determine locations of one or more abnormal heartbeats in the first set number of single heartbeats through the first convolutional neural network.

According to a fifth aspect of the present application, there is provided a machine readable storage medium, wherein the storage medium stores machine executable instructions configured to perform a method of detecting an ECG signal provided in the first or second aspect as described above.

According to a sixth aspect of the present application, there is provided an electronic device, comprising:

a processor; and a storage medium for storing processor executable instructions, wherein, the processor is configured to perform a method of detecting an ECG signal provided in the first or second aspect as described above.

As can be known from the above technical solutions, since any of the single heartbeats is not isolated in the ECG signal with a continuous time sequence, and is related to its adjacent front and rear single heartbeats, the feature data corresponding to each of the first set number of single heartbeats in the present application can be used to well characterize the pathological characteristics of its represented ECG signal, and with the ECG signal and the first set number of feature data, the pathological category of the ECG signal with the set time length can be well detected.

DETAILED DESCRIPTION OF THE EMBODIMENTS

Figure 1A:
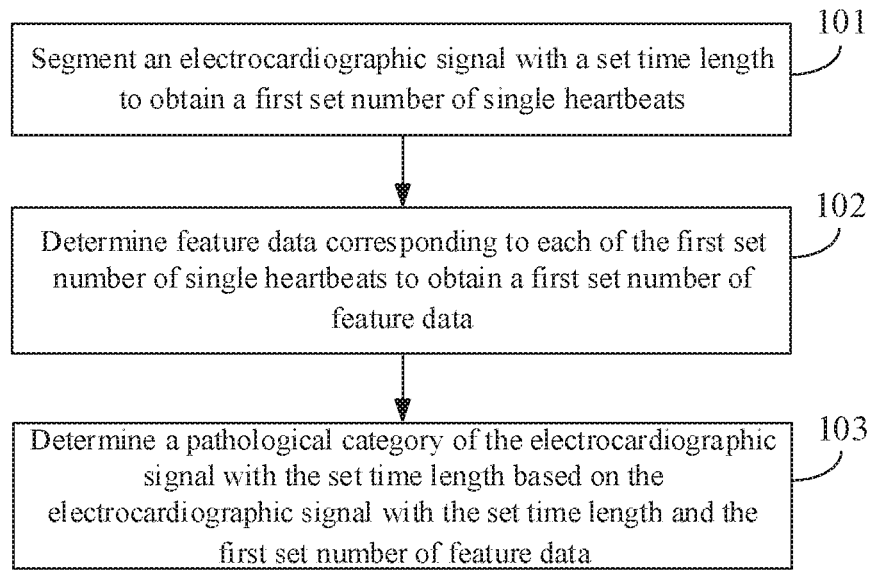
FIG. 1A is a schematic flowchart illustrating a method of detecting an ECG signal according to an example of the present invention.

Examples will be described in detail herein, with the illustrations thereof represented in the drawings. When the following descriptions involve the drawings, like numerals in different drawings refer to like or similar elements unless otherwise indicated. The embodiments described in the following examples do not represent all embodiments consistent with the present disclosure. Rather, they are merely examples of apparatuses and methods consistent with some aspects of the present disclosure as detailed in the appended claims.

The terms used in the present application are for the purpose of describing particular examples only, and are not intended to limit the present application. Terms determined by "a", "the" and "said" in their singular forms in the present application and the appended claims are also intended to include plurality, unless clearly indicated otherwise in the context. It should also be understood that the term "and/or" as used herein refers to and includes any and all possible combinations of one or more of the associated listed items.

It is to be understood that, although terms "first," "second," "third," and the like may be used in the present application to describe various information, such information should not be limited to these terms. These terms are only used to distinguish one category of information from another. For example, without departing from the scope of the present application, first information may be referred as second information; and similarly, second information may also be referred as first information. Depending on the context, the word "if" as used herein may be interpreted as "when" or "upon" or "in response to determining".

To further illustrate the present application, the following examples are provided.

Figure 1B:
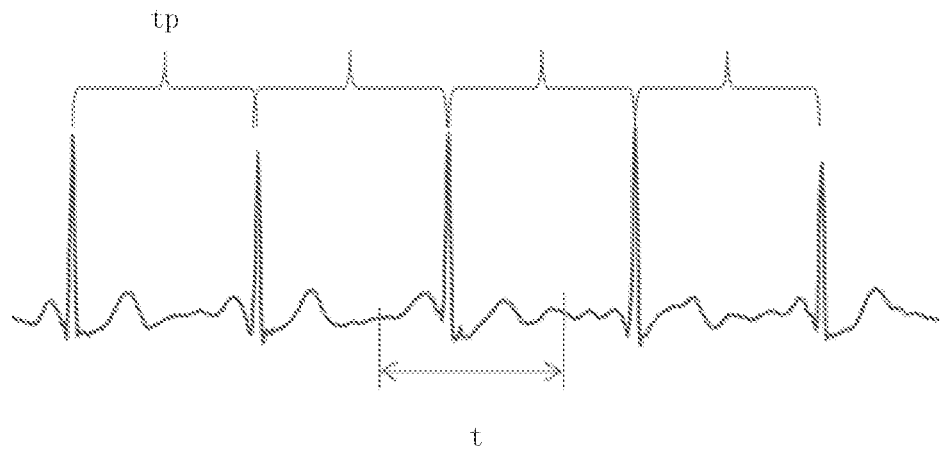
FIG. 1B is a schematic diagram illustrating a continuous ECG signal in the example shown in FIG. 1A.
Figure 1C:
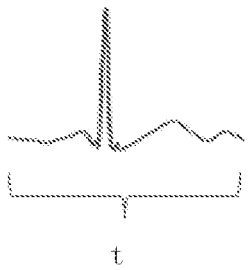
FIG. 1C is a schematic diagram illustrating a single heartbeat in the example shown in FIG. 1A.

FIG. 1A is a schematic flowchart illustrating a method of detecting an ECG signal according to an example of the present invention. FIG. 1B is a schematic diagram illustrating a continuous ECG signal in the example shown in FIG. 1A. FIG. 1C is a schematic diagram illustrating an ECG single heartbeat in the example shown in FIG. 1A. The present application may be applied to an electronic device such as a wearable device and a handheld device to monitor health condition of a heart of a user. As shown in FIG. 1A, the following steps are included:

At step 101, an ECG signal with a set time length is segmented to obtain a first set number of single heartbeats.

In an example, the ECG signal with the set time length may be segmented by a method of identifying an ECG signal to obtain the first set number of single heartbeats. As shown in FIGS. 1B and 1C, by segmenting a continuous ECG signal with a set time length, it is possible to know a start time point, an end time point, and a duration of each single heartbeat, and a duration t of a single heartbeat may be normalized to a preset length. For example, if the preset length is L, the single heartbeat may be expressed as:

$$e=(P,X)=((p_1, p_2, \ldots, p_L),t).$$

where, during the normalization of the duration of the single heartbeat, sampling may be performed at a fixed sample rate. P indicates signal strength of the single heartbeat at each sampling point. For example, $P_1$ indicates signal strength of the single heartbeat at a first sampling point. $P_L$ indicates signal strength of the single heartbeat at an $L^{th}$ sampling point. $p_1, p_2, \ldots, p_L$ indicate signal strength of the single heartbeat at L sampling points. t is the duration of the single heartbeat. Taking the first set number being N as an example, N continuous ECG single heartbeats may be expressed as:

$$E=\{e_1, e_2, \ldots, e_N\}=\{P_1, P_2, \ldots, P_N, t_1, t_2, \ldots, t_N\}=\{(p_{11}, p_{12}, \ldots, p_{1L}), (p_{21}, p_{22}, \ldots, p_{2L}), \ldots, (p_{N1}, p_{N2}, \ldots, p_{NL}), t_1, t_2, \ldots, t_N\}.$$

where, $p_{ij}$ indicates signal strength of an $i^{th}$ single heartbeat at a $j^{th}$ sampling point, wherein, i=1,2, . . . , N, j=1,2, . . . , L, and $t_1, t_2, \ldots, t_N$ indicate the respective duration of N single heartbeats.

At step 102, feature data corresponding to each of the first set number of single heartbeats is determined to obtain a first set number of feature data In an example, the feature data corresponding to each of the first set number of single heartbeats may be determined based on a deep learning network, and the feature data may be a single feature or a combination of multiple features. A single heartbeat signal may be input to the deep learning network, and a convolutional layer of the deep learning network is set to perform convolution processing on the single heartbeat signal to obtain feature data.

Corresponding to the step 101, the feature data is, for example, $T_1, T_2, \ldots, T_N$.

That is, the step 102 may implement: $P_i \rightarrow T_i$, where i=1,2, . . . , N.

At step 103, a pathological category of the ECG signal with the set time length is determined based on the ECG signal with the set time length and the first set number of feature data.

In an example, the ECG signal with the set time length may be input to an input layer of a convolutional neural network, and the first set number of feature data is input to a convolutional layer of the convolutional neural network.

Through the processing of the convolutional neural network, the pathological category of the ECG signal is determined at an output layer of the convolutional neural network. In an example, the convolutional neural network may be trained by massive ECG signals with various pathological characteristics. By training the convolutional neural network, the convolutional neural network may accurately identify the pathological category of the ECG signal.

In an example, the pathological category may include: atrial premature beats, ventricular premature beats, atrial fibrillation, atrial flutter, supraventricular tachycardia, etc. It should be noted that the above-mentioned pathological categories are only illustrative and cannot form a restriction to the present application.

Since any single heartbeat in the continuous ECG signal is not isolated, but is related to its adjacent front and rear single heartbeats, the feature data corresponding to each of the first set number of single heartbeats in the present application can be used to well characterize the pathological characteristics of its represented ECG signal, and therefore with the ECG signal and the first set number of feature data, the pathological category of the ECG signal with the set time length can be well detected.

Figure 2A:
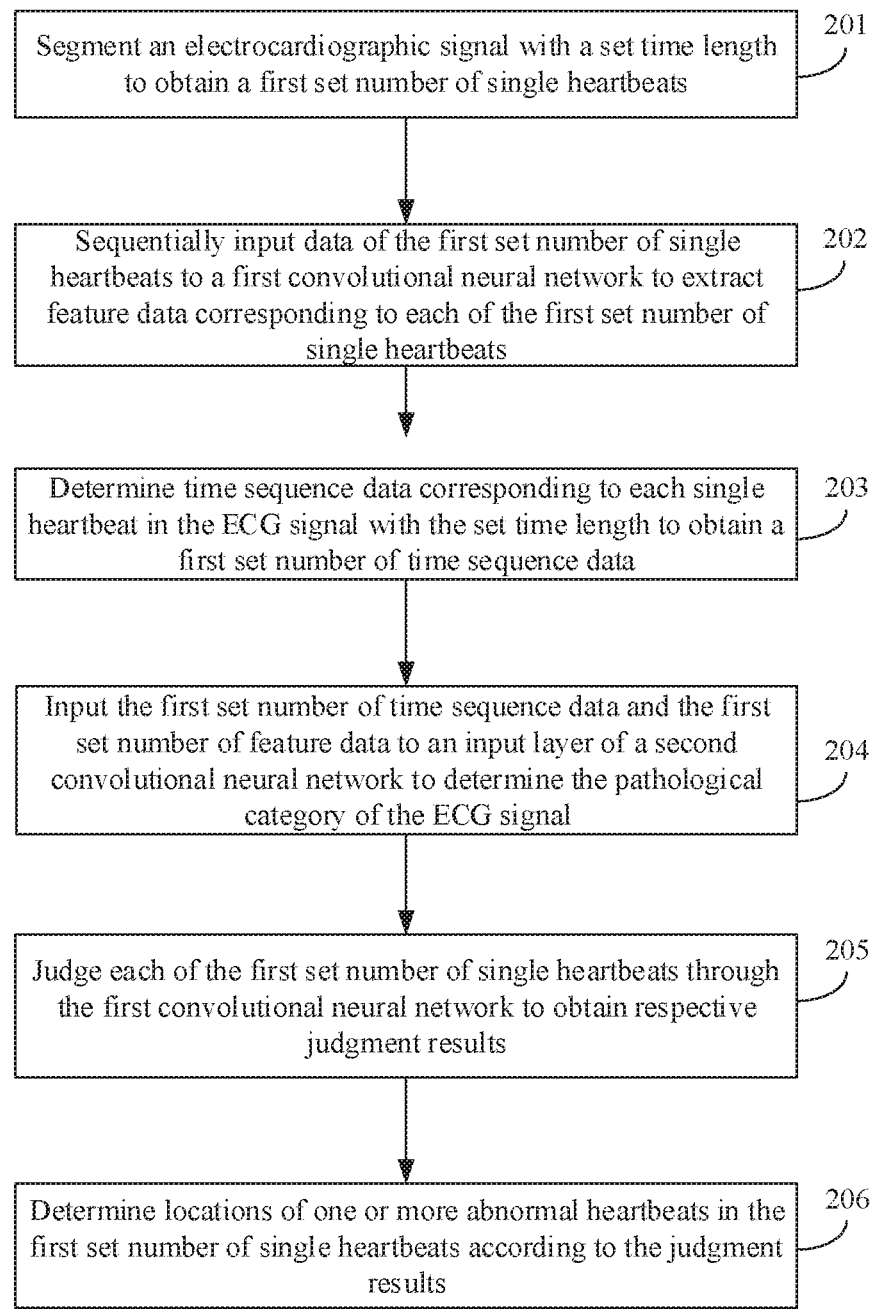
FIG. 2A is a schematic flowchart illustrating a method of detecting an ECG signal according to another example of the present invention.
Figure 2B:
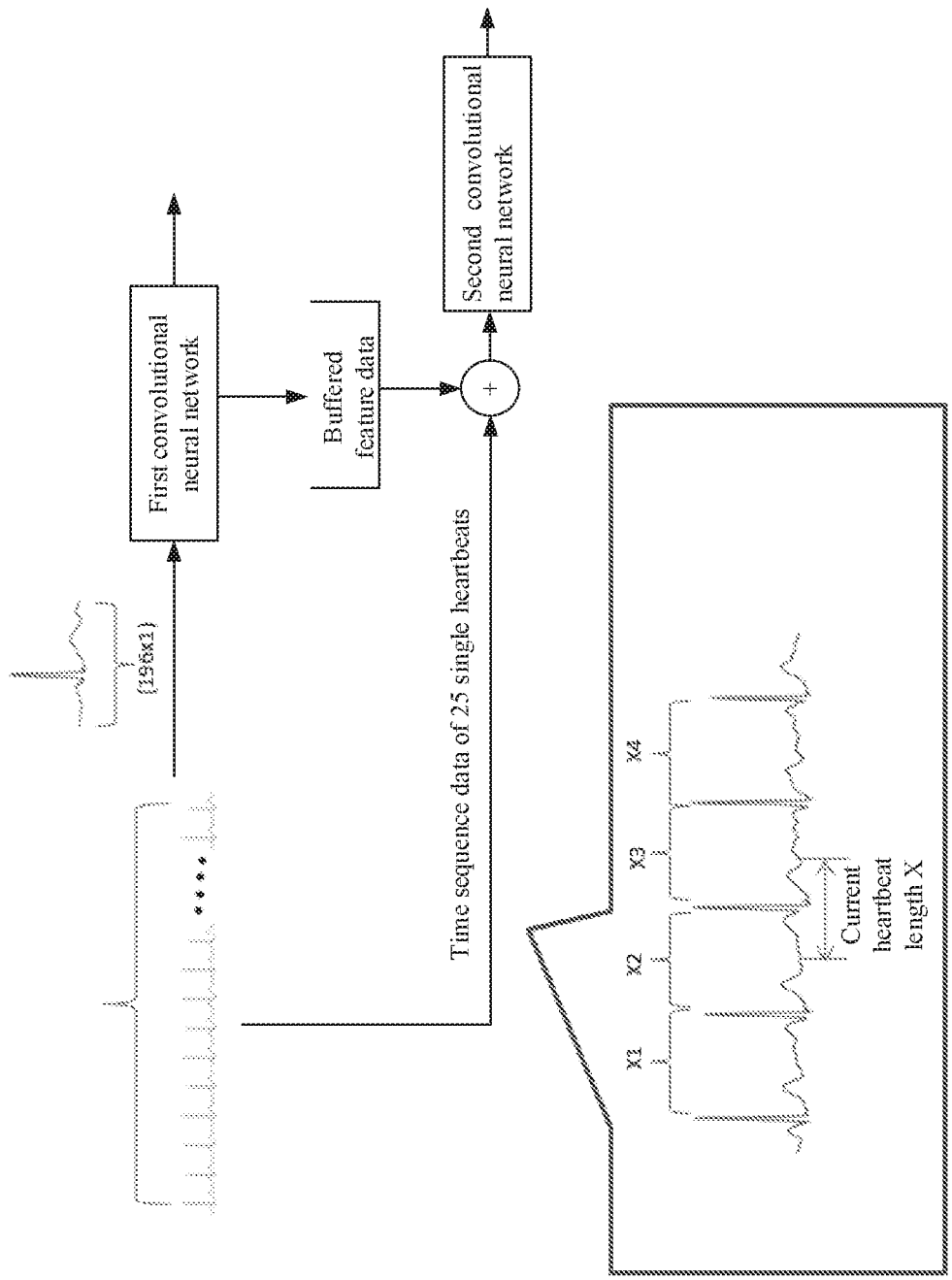
FIG. 2B is a schematic diagram illustrating a structure of detecting an ECG signal applicable to the example shown in FIG. 2A.
Figure 2C:
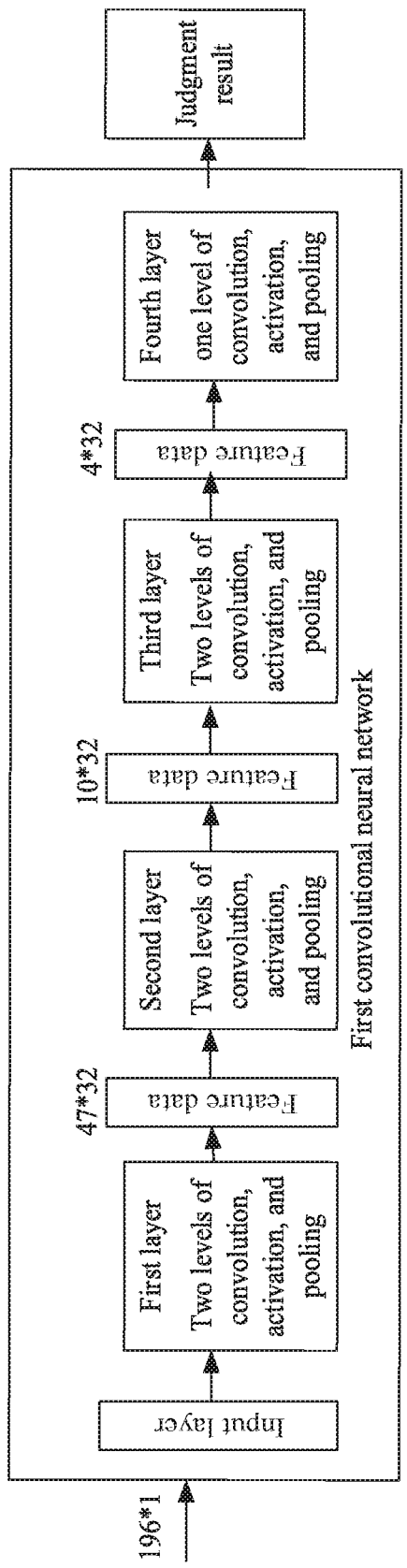
FIG. 2C is a schematic diagram illustrating a structure of a first convolutional neural network in the example shown in FIG. 2A.
Figure 2D:
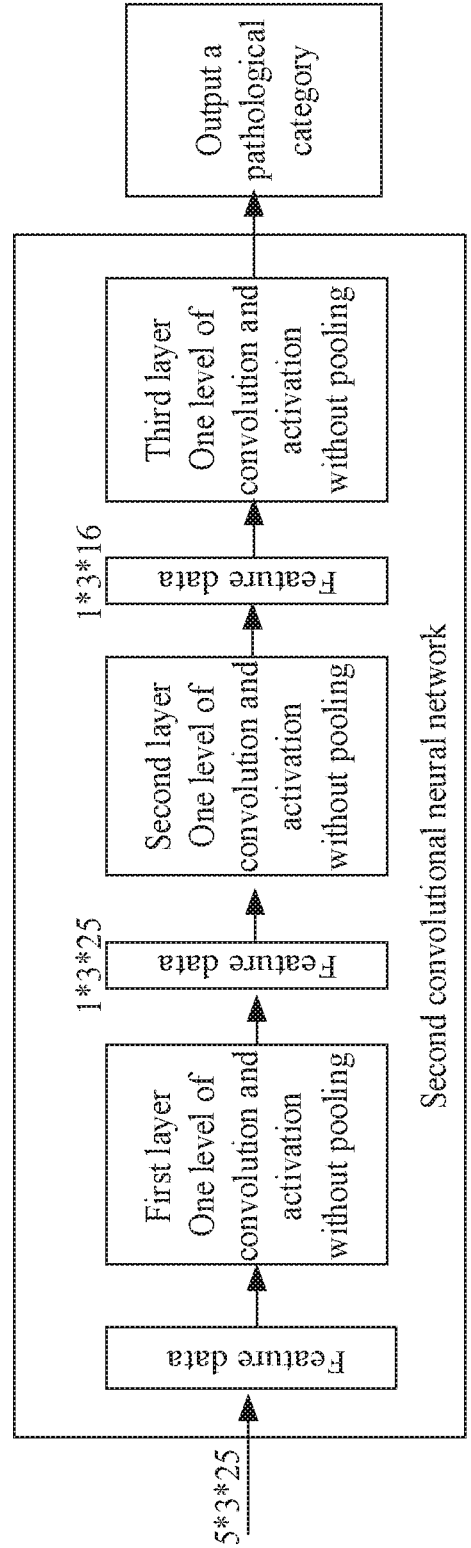
FIG. 2D is a schematic diagram illustrating a structure of a second convolutional neural network in the example shown in FIG. 2A.

FIG. 2A is a schematic flowchart illustrating a method of detecting an ECG signal according to another example of the present invention. FIG. 2B is a schematic diagram illustrating a structure of detecting an ECG signal applicable to the example shown in FIG. 2A. FIG. 2C is a schematic diagram illustrating a structure of a first convolutional neural network in the example shown in FIG. 2A. FIG. 2D is a schematic diagram illustrating a structure of a second convolutional neural network in the example shown in FIG. 2A. As shown in FIG. 2A, the following steps are included:

At step 201, an ECG signal with a set time length is segmented to obtain a first set number of single heartbeats.

For the description of the step 201, reference may be made to the description of the example shown in FIG. 1A, which will not be described in detail herein.

At step 202, data of the first set number of single heartbeats is sequentially input to a first convolutional neural network to extract the feature data corresponding to each of the first set number of single heartbeats.

At step 203, time sequence data corresponding to each single heartbeat in the ECG signal with the set time length is determined to obtain a first set number of time sequence data.

At step 204, the first set number of time sequence data and the first set number of feature data are input to an input layer of a second convolutional neural network to determine a pathological category of the ECG signal.

At step 205, each of the first set number of single heartbeats is judged through the first convolutional neural network to obtain respective judgment results.

At step 206, locations of one or more abnormal heartbeats in the first set number of single heartbeats are determined according to the judgment results.

It should be noted that the steps 205 and 206 are not necessarily performed after the step 204, and may also be performed after the step 202, so that the locations of the one or more abnormal heartbeat in the first set number of single heartbeats may be identified through the first convolutional neural network.

Hereinafter, the example will be illustrated with reference to FIGS. 2B-2D.

At the step 202, as shown in FIG. 2B, 25 continuous single heartbeats as well as respective start time points, respective end time points and respective duration of the 25 single heartbeats are obtained and length normalization is performed on data of each single heartbeat through the step 201, for example, the normalized length is 196, then the data of the 25 single heartbeats with the length of 196 may be sequentially input to the first convolutional neural network. Feature data corresponding to each single heartbeat may be output at a preset convolutional layer of the first convolutional neural network. For example, if each single heartbeat corresponds to 5*2 feature data, the 25 single heartbeats may correspond to 5*2*25 feature data. As shown in FIG. 2B, after obtaining the feature data of each single heartbeat through the first convolutional neural network, the feature data corresponding to each single heartbeat may be buffered.

At the steps 203 and 204, in an example, it is possible to determine a time point corresponding to an R wave of a single heartbeat for each single heartbeat in the ECG signal with the set time length, time points corresponding to respective R waves of a second set number of single heartbeats adjacent to the R wave of the single heartbeat and respectively in the front and at the back of the single heartbeat, and time sequence data corresponding to the single heartbeat based on the time point corresponding to the R wave of the single heartbeat and the time points corresponding to the respective R waves of the second set number of single heartbeats adjacent to the R wave of the single heartbeat and respectively in the front and at the back of the single heartbeat. For example, if the second set number is 2, a distance between the R wave of a current single heartbeat and the R waves of its two front and two rear single heartbeats, i.e., four single heartbeats in total, is $x_1$, $x_2$, $x_3$, $x_4$, respectively. Rhythm information X of each single heartbeat is expressed as a 5-dimensional vector, that is, $$X = \left(t, x_2, x_3, \frac{x_1 + x_2}{2}, \frac{x_4 + x_3}{2}\right) = (t, x_2, x_3, \bar{x}_2, \bar{x}_3),$$

then N single heartbeats may be expressed as:

$E = \{e_1, e_2, \ldots, e_N\} = \{P_1, P_2, \ldots, P_N, X_1, X_2, \ldots X_N\} = \{(p_{11}, p_{12}, \ldots, p_{1L}), (p_{21}, p_{22}, \ldots, p_{2L}), \ldots, (p_{N1}, p_{N2}, \ldots, p_{NL}), (t_1, x_{12}, x_{13}, \bar{x}_{12}, \bar{x}_{13}), (t_2, x_{22}, x_{23}, \bar{x}_{22}, \bar{x}_{23}), \ldots, (t_N, x_{N2}, x_{N3}, \bar{x}_{N2}, \bar{x}_{N3})\}.$ where N is the first set number, that is, the number of the single heartbeats.

For example, if a single heartbeat corresponds to m1*n1 feature data and m2*n2 time sequence data, the amount of data input to the second convolutional neural network may be expressed as m1*n1+m2*n2. As shown in FIG. 2B, the single heartbeats input to the second convolutional neural network correspond to 5*2*25 feature data, and the single heartbeats input to the second convolutional neural network correspond to 5*1*25 time sequence data, then the amount of data input to the second convolutional neural network may be expressed as 5*3*25.

At the step 204, after the second convolutional neural network is trained by massive ECG signals with various pathological characteristics, the second convolutional neural network may accurately identify the pathological category of the ECG signal with the data of the input layer.

At the steps 205 and 206, the first convolutional neural network may be trained by massive ECG signals of normal and abnormal single heartbeats. The first convolutional neural network, after training, may accurately identify whether a single heartbeat is abnormal. For example, after the 25 single heartbeats are sequentially input to the first convolutional neural network, the first convolutional neural network may judge the normality or abnormality of the single heartbeats. For example, if 1 indicates that a single heartbeat is normal, and 0 indicates that a single heartbeat is abnormal, the 25 single heartbeats may correspond to a sequence combination of 0 and 1, the total number of 0 s and 1 s in the sequence combination being 25. Through this sequence combination, locations of one or more abnormal heartbeats in the 25 single heartbeats may be identified.

As shown in FIG. 2C, the first convolutional neural network includes four convolutional layers, each involving processings such as convolution, activation, and pooling. For each convolutional layer, except that the input and output data and the size of convolutional kernels are different, a calculation order of the processings is identical. That is, the data of the single heartbeats, after being input to the first convolutional neural network, is first convolved and activated, then pooled to obtain the feature data output by a convolutional layer where in the first convolutional layer to the third convolutional layer, each layer involves convolution of two continuous levels, activation, and pooling, while the fourth convolutional layer involves convolution of only one level, activation, and pooling. Activation calculation generally uses functions such as sigmoid, tanH, and reLu. In the first convolutional neural network, convolution calculation is used to extract the feature data of the ECG signal, activation calculation is used to improve the nonlinearity, i.e., activity, of the feature data, and pooling calculation is used to reduce the dimension of the feature data.

As shown in FIG. 2D, the second convolutional neural network includes three convolutional layers. For each convolutional layer, except that the input and output data and the size of convolutional kernels are different, the calculation order of the processings is identical. That is, the input data including the time sequence data of the ECG signal, after being input to the second convolutional neural network, is convolved and activated to obtain the feature data output by the convolutional layer. In the first convolutional layer to the third convolutional layer, each layer involves convolution of one level and activation, and does not include pooling.

In this example, while the second convolutional neural network performs pathological diagnosis on the continuous ECG signal, it is also possible to accurately determine the locations of the one or more abnormal heartbeats through the first convolutional neural network. Since the feature data output by the first convolutional neural network may be regarded as an approximation of original single heartbeats, accumulation of the feature data output by the first convolutional neural network to original ECG signal greatly enhances the possibility of identifying the ECG signal.

Figure 3A:
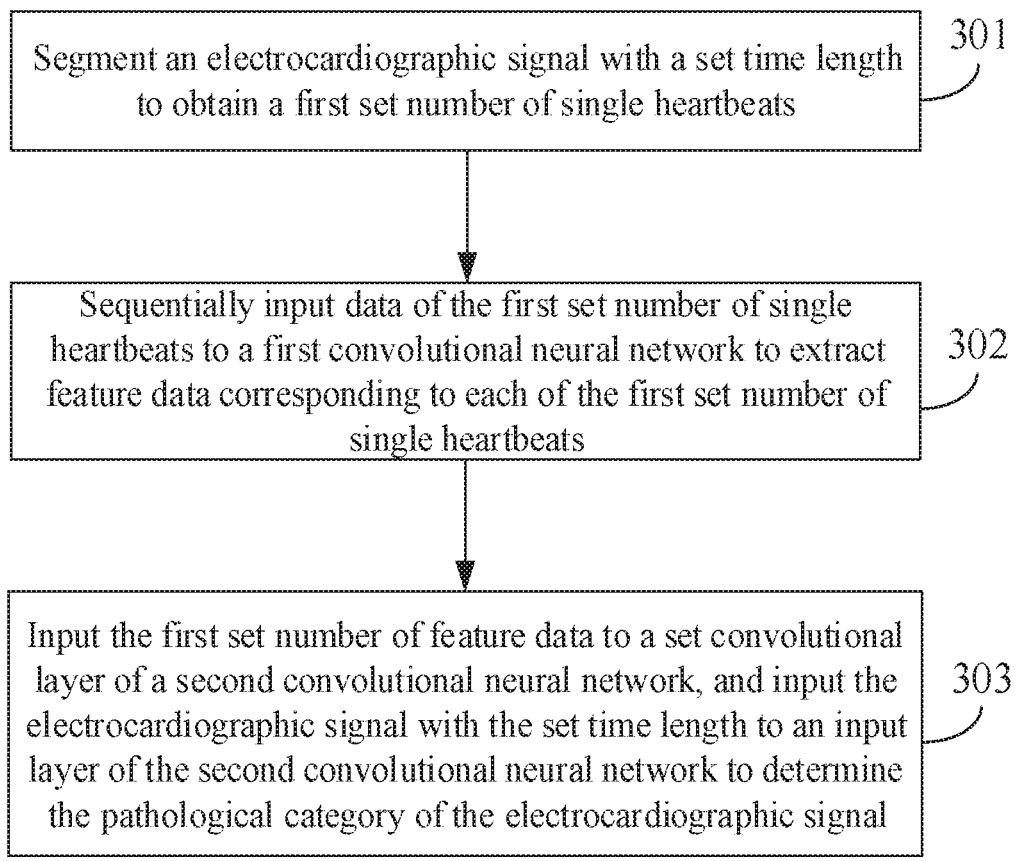
FIG. 3A is a schematic flowchart illustrating a method of detecting an ECG signal according to still another example of the present invention.
Figure 3B:
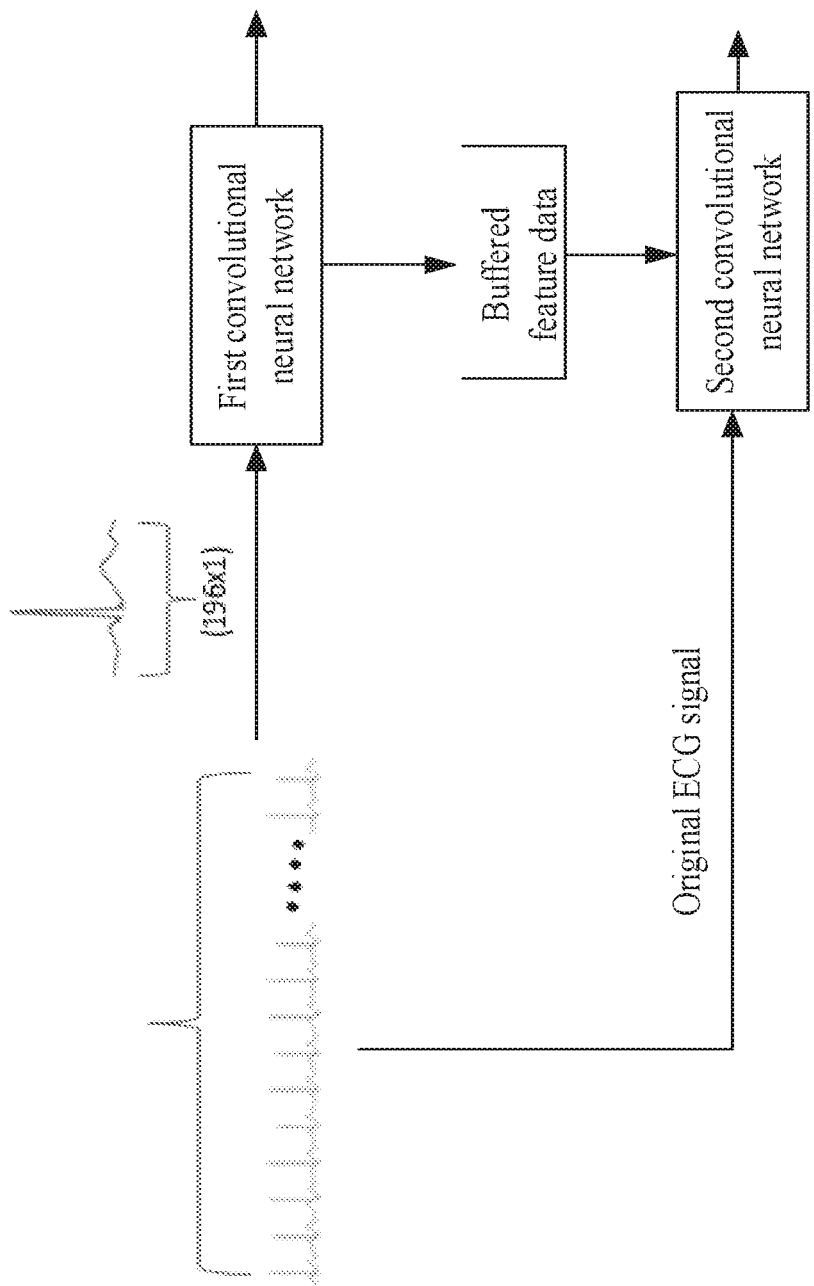
FIG. 3B is a first schematic diagram illustrating a structure of detecting an ECG signal applicable to the example shown in FIG. 3A.
Figure 3C:
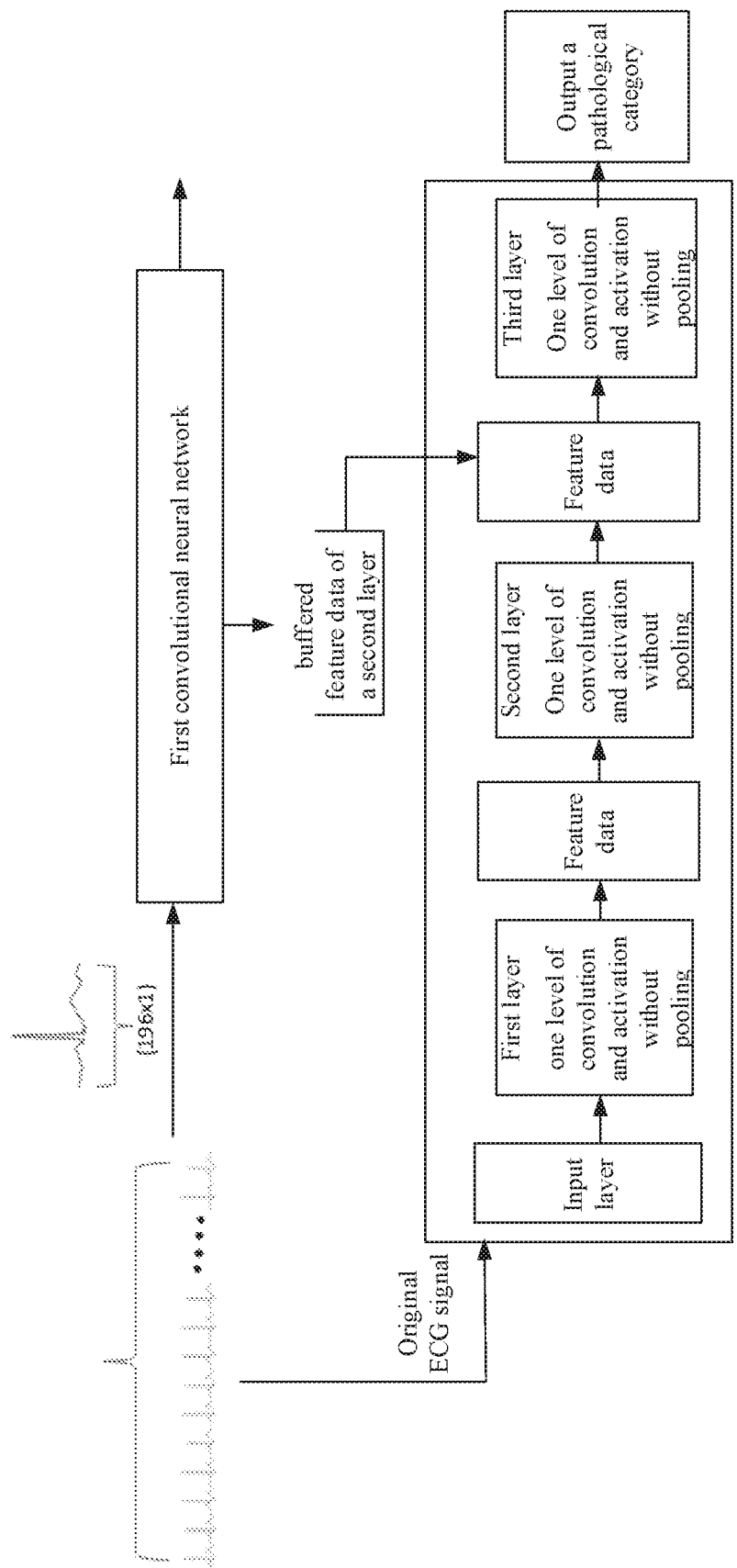
FIG. 3C is a second schematic diagram illustrating a structure of detecting an ECG signal applicable to the example shown in FIG. 3A.

FIG. 3A is a schematic flowchart illustrating a method of detecting an ECG signal according to still another example of the present invention. FIG. 3B is a first schematic diagram illustrating a structure of detecting an ECG signal applicable to the example shown in FIG. 3A. FIG. 3C is a second schematic diagram illustrating a structure of detecting an ECG signal applicable to the example shown in FIG. 3A. As shown in FIG. 3A, the following steps are included:

At step 301, an ECG signal with a set time length is segmented to obtain a first set number of single heartbeats.

For the description of the step 301, reference may be made to the description of the example shown in FIG. 1A, which will not be described herein again.

At step 302, data of the first set number of single heartbeats is sequentially input to a first convolutional neural network to extract the feature data corresponding to each of the first set number of single heartbeats.

For the description of the step 302, reference may be made to the description of the example shown in FIG. 2A, which will not be described herein again.

At step 303, the first set number of feature data is input to a set convolutional layer of a second convolutional neural network, and the ECG signal with the set time length is input to an input layer of the second convolutional neural network to determine a pathological category of the ECG signal through the second convolutional neural network.

For the description of the step 303, reference may be made to the description of the example shown in FIG. 2A, which will not be described herein again.

Hereinafter, the step 303 will be illustrated with reference to FIGS. 3B and 3C. As shown in FIG. 3B, data of the first set number of single heartbeats obtained by segmentation may be sequentially input to the first convolutional neural network, and original ECG signal not segmented is input to the second convolutional neural network. For example, if continuous original ECG signal is segmented into 20 single heartbeats, data of the 20 single heartbeats is sequentially input to the first convolutional neural network. After the data of the 20 single heartbeats enters the first convolutional neural network and is subjected to corresponding processing, the feature data output from a set convolutional layer of the first convolutional neural network may be buffered. For example, 20 sets of feature data output from the second convolutional layer of the first convolutional neural network may be buffered. If the amount of feature data output by each single heartbeat from the second convolutional layer is expressed as 21*32, the amount of feature data corresponding to the 20 single heartbeats may be expressed as 21*32*20=420*32.

The continuous original ECG signal is input to the input layer of the second convolutional neural network.

In an example, the feature data obtained from the set convolutional layer of the first convolutional neural network may be injected into the feature data obtained from a set convolutional layer of the second convolutional neural network. As shown in FIG. 3C, the feature data obtained from the second convolutional layer of the first convolutional neural network is injected into the feature data obtained from the second convolutional layer of the second convolutional neural network, and the two sets of feature data combined are input to the third convolutional layer of the second convolutional neural network. For example, if the amount of feature data obtained from the second convolutional layer of the second convolutional neural network is expressed as 531*32, the amount of feature data input to the third convolutional layer is expressed as 420*32+531*32= (531−111)*32+531*32=531*64−111*32. If the amount of feature data that the third convolutional layer is able to process is expressed as 531*64, for the third convolutional layer, 111*32 feature data is missing. For the missing part, it is possible to ensure the consistency of the feature data actually input to the third convolutional layer with the feature data to be processed by the third convolutional layer by way of zero padding.

It should be noted that FIG. 3C is only illustrative, and feature data with different dimensions may be output from the set convolutional layer of the first convolutional neural network and injected into the set convolutional layer of the second convolutional neural network, so that the dependence of the second convolutional neural network on the feature data of the first convolutional neural network may be flexibly adjusted. The set convolutional layer here may be one convolutional layer or a plurality of convolutional layers. For example, feature data output from the second convolutional layer of the first convolutional neural network may be injected into the second convolutional layer of the second convolutional neural network, and at the same time, the feature data output from the third convolutional layer of the first convolutional neural network is injected into the third convolutional layer of the second convolutional neural network.

In this example, by inputting the feature data output from the set convolutional layer of the first convolutional neural network to the set convolutional layer of the second convolutional neural network, the identification result from the second convolutional neural network may be dependent on the feature data of the first convolutional neural network so as to enhance the identification performance for the ECG signals.

Figure 4A:
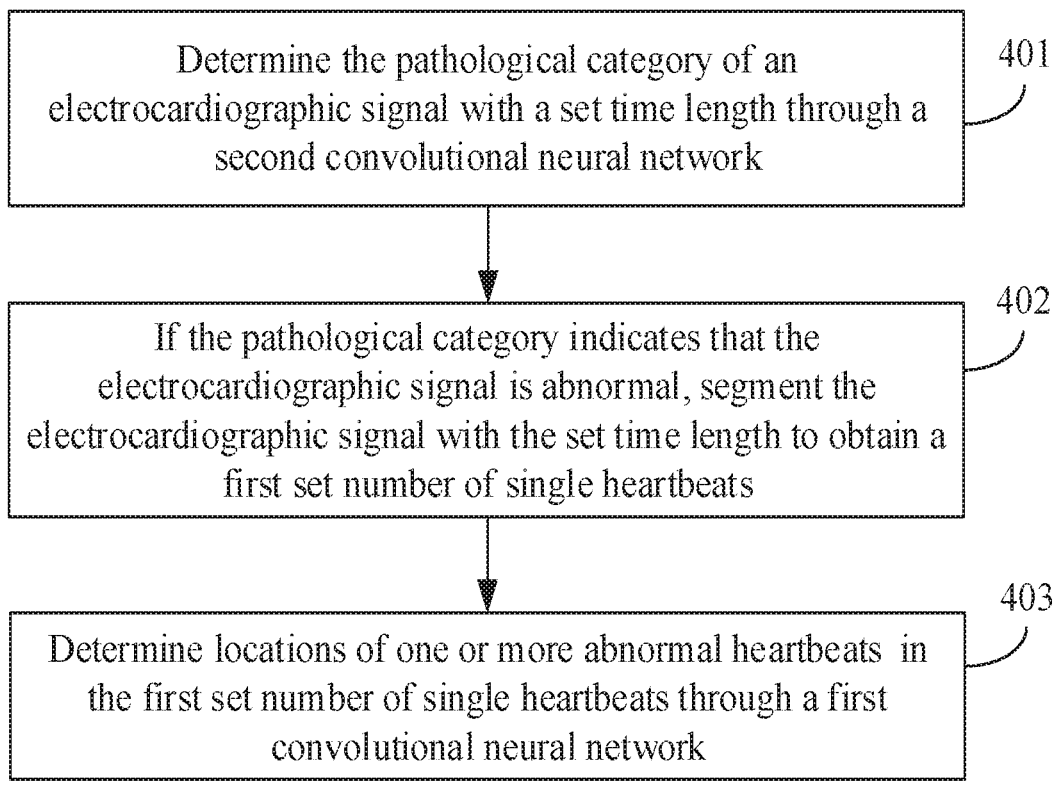
FIG. 4A is a schematic flowchart illustrating a method of detecting an ECG signal according to yet another example of the present invention.
Figure 4B:
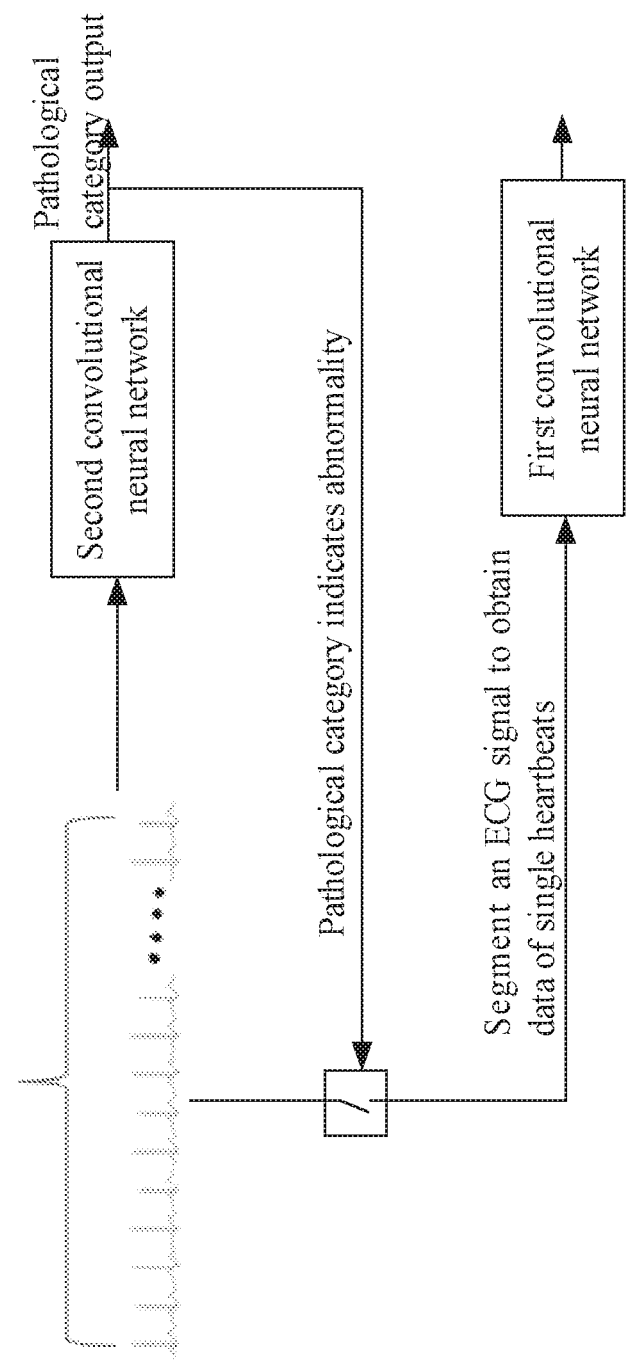
FIG. 4B is a schematic diagram illustrating a structure of detecting an ECG signal applicable to the example shown in FIG. 4A.

FIG. 4A is a schematic flowchart illustrating a method of detecting an ECG signal according to yet another example of the present invention. FIG. 4B is a schematic diagram illustrating a structure of detecting an ECG signal applicable to the example shown in FIG. 4A. As shown in FIG. 4A, the following steps are included:

At step 401, an ECG signal with a set time length is input to a second convolutional neural network, and a pathological category of the ECG signal is determined through the second convolutional neural network.

At step 402, if the pathological category indicates that the ECG signal is abnormal, the ECG signal with the set time length is segmented to obtain a first set number of single heartbeats.

At step 403, data of the obtained first set number of single heartbeats is input to a first convolutional neural network, and locations of one or more abnormal heartbeats in the first set number of single heartbeats are determined through the first convolutional neural network.

Optionally, at the step 403, it is possible to input the data of the first set number of single heartbeats to an input layer of the first convolutional neural network, judge each of the first set number of single heartbeats through the first convolutional neural network to obtain respective judgment results, and determine locations of one or more abnormal heartbeats in the first set number of single heartbeats according to the judgment results.

As shown in FIG. 4B, data of a segment of continuous ECG signal with a set time length, for example, 30 seconds, is directly input to the second convolutional neural network, and the data of the continuous ECG signal is identified to obtain a pathological category. If the pathological category indicates that the ECG signal is abnormal, the ECG signal may be segmented to obtain, for example, data of 25 single heartbeats. The data of the 25 single heartbeats is sequentially input to the first convolutional neural network for identification, and the respective judgment results are obtained. The judgment results may be a sequence consisting of 0 and 1. For example, if 0 indicates abnormality, and 1 indicates normality, the 25 single heartbeats may correspond to a combination of 0 and 1 with a length of 25 bits. By identifying the location where 0 is, the locations of the one or more abnormal heartbeats in the 25 single heartbeats may be determined.

In this example, when the pathological category identified by the second convolutional neural network indicates that the ECG signal is abnormal, the single heartbeats of the ECG signal are identified, one by one, through the first convolutional neural network so as to identify the locations of the one or more abnormal heartbeats.

As can be known from the structural diagrams shown in FIGS. 2B, 3A, 3B and 4B, the first convolutional neural network in the present application may be regarded as a single heartbeat identification network, and the second convolutional neural network may be regarded as an ECG signal detection network. The structural designs of the first convolutional neural network and the second convolutional neural network in the present application may have the following beneficial technical effects:

1) the first convolutional neural network may be trained separately to reduce the difficulty of training the entire network structure;

2) it is easy to obtain sufficient single heartbeat data as a training sample of the first convolutional neural network, so that the first convolutional neural network may be fully trained, and the stability and reliability of single heartbeat identification may be guaranteed;

3) the training of the second convolutional neural network may be enhanced based on the feature data obtained by the first convolutional neural network, so that the problem of insufficient data of the ECG signal of continuous heartbeats with a long sequence may be solved;

4) because of a small number of ECG signals, the structural design in the present application may be applied to an embedded development application.

Figure 5:
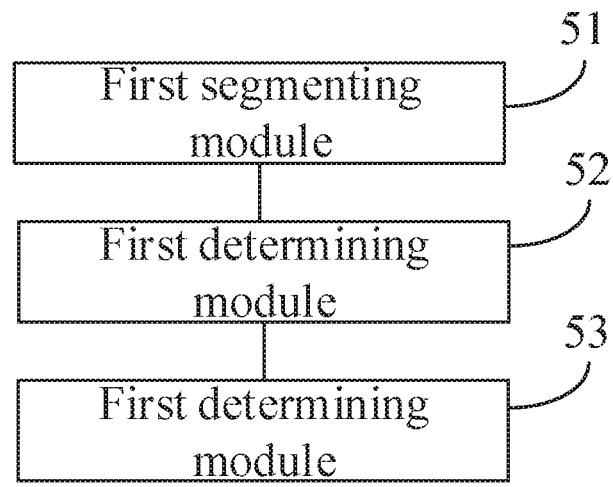
FIG. 5 is a schematic diagram illustrating a structure of an apparatus for detecting an ECG signal according to an example of the present invention.

FIG. 5 is a schematic diagram illustrating a structure of an apparatus for detecting an ECG signal according to an example of the present invention. As shown in FIG. 5, the apparatus for detecting the ECG signal may include: a first segmenting module 51, a first determining module 52, and a second determining module 53.

The first segmenting module 51 is configured to segment an ECG signal with a set time length to obtain a first set number of single heartbeats.

The first determining module 52 is configured to determine feature data corresponding to each of the first set number of single heartbeats obtained by the first segmenting module 51 to obtain a first set number of feature data.

The second determining module 53 is configured to determine a pathological category of the ECG signal with the set time length based on the ECG signal with the set time length and the first set number of feature data determined by the first determining module 52.

Figure 6:
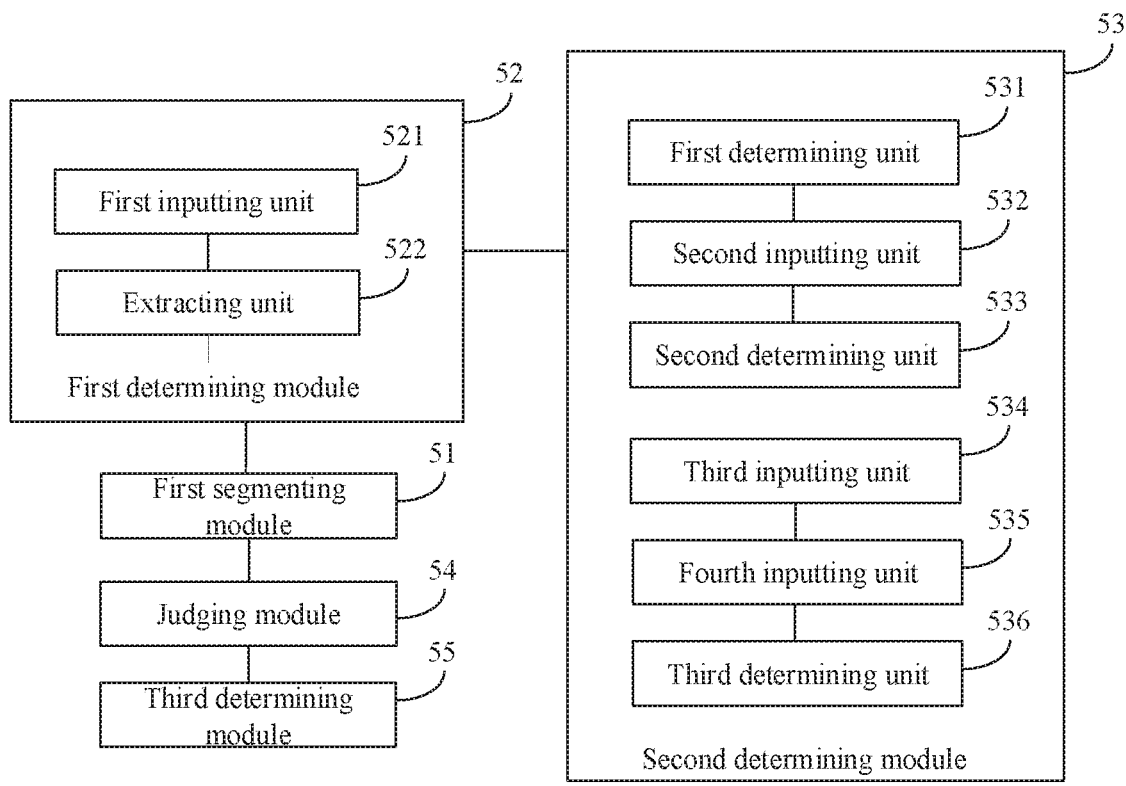
FIG. 6 is a schematic diagram illustrating a structure of an apparatus for detecting an ECG signal according to another example of the present invention.

FIG. 6 is a schematic diagram illustrating a structure of an apparatus for detecting an ECG signal according to another example of the present invention. As shown in FIG. 6, based on the example shown in FIG. 5, the first determining module 52 may include:

a first inputting unit 521 configured to sequentially input data of the first set number of single heartbeats to a first convolutional neural network; and an extracting unit 522 configured to extract the feature data corresponding to each of the first set number of single heartbeats through the first convolutional neural network.

In an example, the apparatus for detecting the ECG signal further includes:

a judging module 54 configured to judge each of the first set number of single heartbeats obtained by the first segmenting module 51 through the first convolutional neural network to obtain respective judgment results; and a third determining module 55 configured to determine locations of one or more abnormal heartbeats in the first set number of single heartbeats according to the judgment results obtained by the judging module 54.

In an example, the second determining module 53 may include:

a first determining unit 531 configured to determine time sequence data corresponding to each of the first set number of single heartbeats to obtain a first set number of time sequence data;

a second inputting unit 532 configured to input the first set number of time sequence data obtained by the first determining unit 531 and the first set number of feature data to an input layer of a second convolutional neural network; and a second determining unit 533 configured to determine the pathological category of the ECG signal through the second convolutional neural network.

The first determining unit 531 may be specifically configured to:

for each single heartbeat in the ECG signal with the set time length, determine a time point corresponding to an R wave of the single heartbeat;

determine time points corresponding to respective R waves of a second set number of single heartbeats adjacent to the R wave of the single heartbeat and respectively in the front and at the back of the single heartbeats; and determine the time sequence data corresponding to the single heartbeat based on the time point corresponding to the R wave of the single heartbeat and the time points corresponding to the respective R waves of the second set number of single heartbeats adjacent to the R wave of the single heartbeat and respectively in the front and at the back of the single heartbeats.

In an example, the second determining module 53 includes:

a third inputting unit 534 configured to input the first set number of feature data to a set convolutional layer of a second convolutional neural network;

a fourth inputting unit 535 configured to input the ECG signal with the set time length to an input layer of the second convolutional neural network; and a third determining unit 536 configured to identify the first set number of feature data input by the third inputting unit 534 and the ECG signal input by the fourth inputting unit 535 through the second convolutional neural network to determine the pathological category of the ECG signal.

Figure 7:
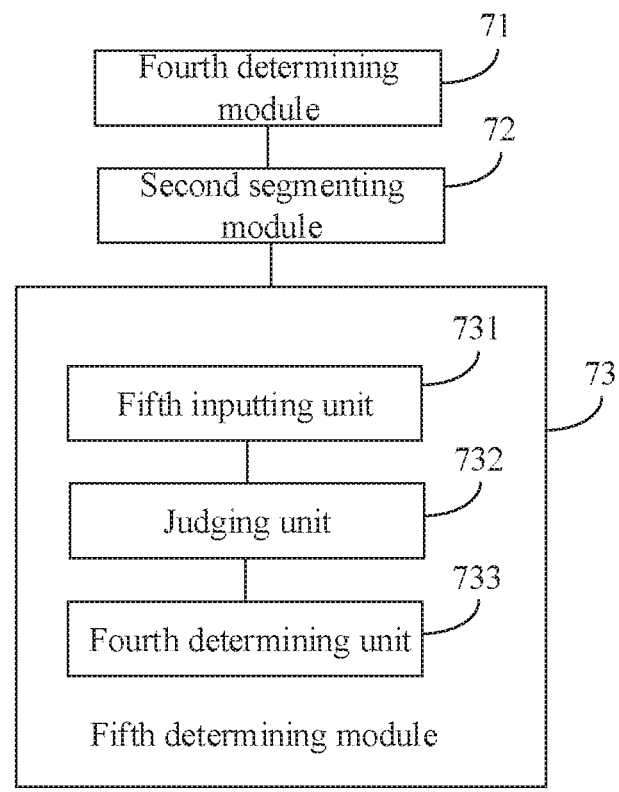
FIG. 7 is a schematic diagram illustrating a structure of an apparatus for detecting an ECG signal according to still another example of the present invention.

FIG. 7 is a schematic diagram illustrating a structure of an apparatus for detecting an ECG signal according to still another example of the present invention. As shown in FIG. 7, the apparatus for detecting the ECG signal may include: a fourth determining module 71, a second segmenting module 72, and a fifth determining module 73.

The fourth determining module 71 is configured to determine a pathological category of an ECG signal with a set time length through a second convolutional neural network.

The second segmenting module 72 is configured to, if the pathological category determined by the fourth determining module 71 indicates that the ECG signal is abnormal, segment the ECG signal with the set time length to obtain a first set number of single heartbeats.

The fifth determining module 73 is configured to input data of the first set number of single heartbeats obtained by the second segmenting module 72 to a first convolutional neural network to determine locations of one or more abnormal heartbeats in the first set number of single heartbeats through the first convolutional neural network.

In an example, the fifth determining module 73 may include:

a fifth inputting unit 731 configured to input the data of the first set number of single heartbeats to an input layer of the first convolutional neural network;

a judging unit 732 configured to judge each of the first set number of single heartbeats input by the fifth inputting unit 731 to the first convolutional neural network to obtain respective judgment results; and a fourth determining unit 733 configured to determine the locations of the one or more abnormal heartbeats in the first set number of single heartbeats according to the judgment results obtained by the judging unit 732.

Figure 8:
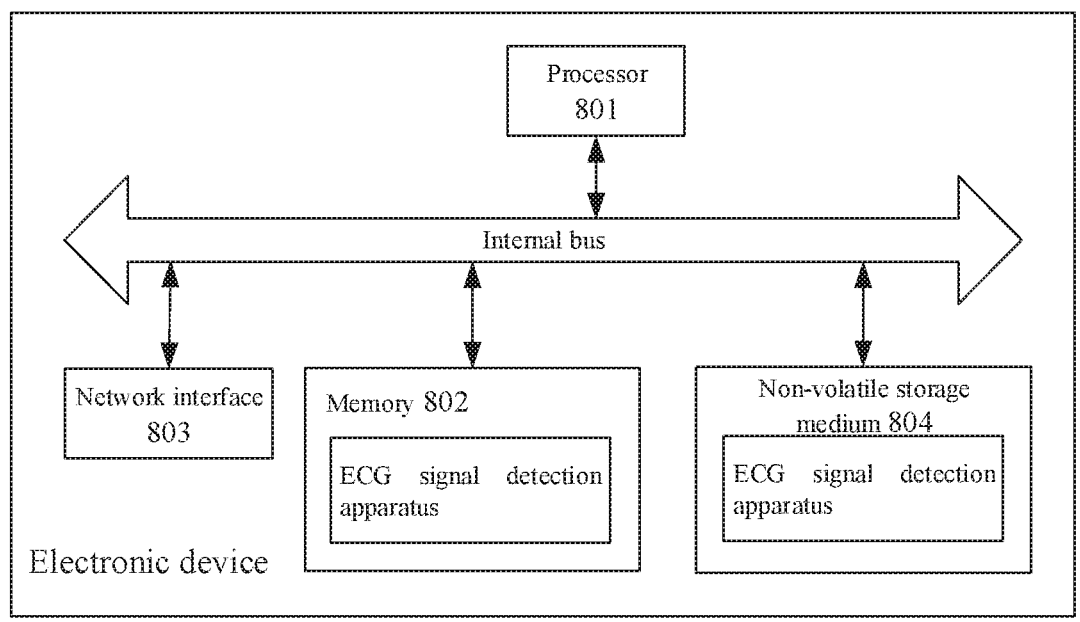
FIG. 8 is a schematic diagram illustrating a structure of an electronic device according to an example of the present invention.

The examples of an apparatus for detecting an electrocardiographic signal according to the present application may be applied to an electronic device. The apparatus examples may be implemented by software or by hardware or by a combination of software and hardware. Taking software implementation as an example, as a logical apparatus, it is formed by a processor of an electronic device, where it is located, reading corresponding machine executable instructions in a non-volatile storage medium into a memory for execution. In terms of hardware, as shown in FIG. 8, which is a diagram illustrating a hardware structure of an electronic device where the ECG signal detection apparatus according to the present application is located, in addition to a processor 801, a memory 802, a network interface 803, and a non-volatile storage medium 804 as shown in FIG. 8, the electronic device where the apparatus is located in the examples may usually further include other hardware according to the actual function of the electronic device, which will not be described herein again.

Other embodiments of the present application will be readily apparent to those skilled in the art after considering the specification and practicing the contents disclosed herein. The present application is intended to cover any variations, uses, or adaptations of the present application, which follow the general principle of the present application and include common knowledge or conventional technical means in the art that are not disclosed in the present application. The specification and examples are to be regarded as illustrative only. The true scope and spirit of the present application are pointed out by the following claims.

It should also be noted that the term "including", "containing" or any variation thereof is intended to encompass non-exclusive inclusion, so that a process, method, article or device including a series of elements includes not only those elements but also other elements not listed explicitly or those elements inherent to such a process, method, article or device. Without more limitations, an element defined by the statement "including a . . . " shall not be precluded to include additional same elements present in a process, method, article or device including the elements.

The above are only the preferred examples of the present application, which are not intended to limit the present application, and any modifications, equivalent substitutions, improvements thereof, etc. made within the spirit and principles of the present application should be included in the protection scope of the present application.

The invention claimed is:

1. A method of detecting an electrocardiographic signal, comprising:

segmenting an electrocardiographic signal with a set time length to obtain a first set number of single heartbeats;

determining feature data corresponding to each of the first set number of single heartbeats to obtain a first set number of feature data; and determining a pathological category of the electrocardiographic signal with the set time length based on the electrocardiographic signal with the set time length and the first set number of feature data, wherein determining the feature data corresponding to each of the first set number of single heartbeats comprises:
sequentially inputting data of the first set number of single heartbeats to a first convolutional neural network; and
extracting the feature data corresponding to each of the first set number of single heartbeats through the first convolutional neural network, and
wherein determining the pathological category of the electrocardiographic signal with the set time length based on the electrocardiographic signal with the set time length and the first set number of feature data comprises:
inputting the first set number of feature data to a set convolutional layer of a second convolutional neural network;
inputting the electrocardiographic signal with the set time length to an input layer of the second convolutional neural network; and
determining the pathological category of the electrocardiographic signal through the second convolutional neural network.

2. The method according to claim 1, further comprising:
judging each of the first set number of single heartbeats through the first convolutional neural network to obtain respective judgment results; and
determining locations of one or more abnormal heartbeats in the first set number of single heartbeats according to the judgment results.

3. The method according to claim 1,
wherein determining the pathological category of the electrocardiographic signal with the set time length based on the electrocardiographic signal with the set time length and the first set number of feature data comprises:
determining time sequence data corresponding to each of the first set number of single heartbeats respectively to obtain a first set number of time sequence data; and
inputting the first set number of time sequence data and the first set number of feature data to an input layer of a second convolutional neural network to determine the pathological category of the electrocardiographic signal through the second convolutional neural network.

4. The method according to claim 3,
wherein determining the time sequence data corresponding to each of the first set number of single heartbeats comprises:
determining a time point corresponding to an R wave of the single heartbeat;
determining time points corresponding to respective R waves of a second set number of single heartbeats adjacent to the R wave of the single heartbeat and respectively in the front and at the back of the single heartbeat; and
determining the time sequence data corresponding to the single heartbeat based on the time point corresponding to the R wave of the single heartbeat and the time points corresponding to the respective R waves of the second set number of single heartbeats adjacent to the R wave of the single heartbeat and respectively in the front and at the back of the single heartbeat.

5. A method of detecting an electrocardiographic signal, comprising:
segmenting an electrocardiographic signal with a set time length to obtain a first set number of single heartbeats;
determining feature data corresponding to each of the first set number of single heartbeats to obtain a first set number of feature data; and
determining a pathological category of the electrocardiographic signal with the set time length based on the electrocardiographic signal with the set time length and the first set number of feature data,
wherein determining the feature data corresponding to each of the first set number of single heartbeats comprises:
sequentially inputting data of the first set number of single heartbeats to a first convolutional neural network; and
extracting the feature data corresponding to each of the first set number of single heartbeats through the first convolutional neural network,
wherein determining the pathological category of the electrocardiographic signal with the set time length based on the electrocardiographic signal with the set time length and the first set number of feature data comprises:
inputting the first set number of feature data to a set convolutional layer of a second convolutional neural network;
inputting the electrocardiographic signal with the set time length to an input layer of the second convolutional neural network; and
determining the pathological category of the electrocardiographic signal through the second convolutional neural network, and
wherein the method further comprises:
if the pathological category indicates that the electrocardiographic signal is abnormal,
inputting the data of the first set number of single heartbeats to the first convolutional neural network to determine locations of one or more abnormal heartbeats in the first set number of single heartbeats through the first convolutional neural network.

6. The method according to claim 5,
wherein determining the locations of the one or more abnormal heartbeats in the first set number of single heartbeats through the first convolutional neural network comprises:
inputting the data of the first set number of single heartbeats to an input layer of the first convolutional neural network to judge each of the first set number of single heartbeats through the first convolutional neural network to obtain respective judgment results; and
determining the locations of the one or more abnormal heartbeats in the first set number of single heartbeats according to the judgment results.

7. An apparatus for detecting an electrocardiographic signal, comprising:
a processor; and
a storage medium for storing processor executable instructions,
wherein, the processor is configured to:
segment an electrocardiographic signal with a set time length to obtain a first set number of single heartbeats;
determine feature data corresponding to each of the first set number of single heartbeats to obtain a first set number of feature data; and
determine a pathological category of the electrocardiographic signal with the set time length based on the electrocardiographic signal with the set time length and the first set number of feature data, wherein when determining the feature data corresponding to each of the first set number of single heartbeats, the processor is configured to:

sequentially input data of the first set number of single heartbeats to a first convolutional neural network; and extract the feature data corresponding to each of the first set number of single heartbeats through the first convolutional neural network, and wherein when determining the pathological category of the electrocardiographic signal with the set time length based on the electrocardiographic signal with the set time length and the first set number of feature data, the processor is configured to:

input the first set number of feature data to a set convolutional layer of a second convolutional neural network;

input the electrocardiographic signal with the set time length to an input layer of the second convolutional neural network; and identify the first set number of feature data and the electrocardiographic signal through the second convolutional neural network to determine the pathological category of the electrocardiographic signal.

8. The apparatus according to claim 7,
wherein the processor is further configured to:
judge each of the first set number of single heartbeats through the first convolutional neural network to obtain respective judgment results; and
determine locations of one or more abnormal heartbeats in the first set number of single heartbeats according to the judgment results.

9. The apparatus according to claim 7,
wherein when determining the pathological category of the electrocardiographic signal with the set time length based on the electrocardiographic signal with the set time length and the first set number of feature data, the processor is configured to:
determine time sequence data corresponding to each of the first set number of single heartbeats to obtain a first set number of time sequence data;
input the first set number of time sequence data and the first set number of feature data to an input layer of a second convolutional neural network; and
determine the pathological category of the electrocardiographic signal through the second convolutional neural network.

10. The apparatus according to claim 9, wherein when determining the time sequence data corresponding to each of the first set number of single heartbeats, the processor is configured to:
determine a time point corresponding to an R wave of the single heartbeat;
determine time points corresponding to respective R waves of a second set number of single heartbeats adjacent to the R wave of the single heartbeat and respectively in the front and at the back of the single heartbeat; and
determine the time sequence data corresponding to the single heartbeat based on the time point corresponding to the R wave of the single heartbeat and the time points corresponding to the respective R waves of the second set number of single heartbeats adjacent to the R wave of the single heartbeat and respectively in the front and at the back of the single heartbeat.

11. An apparatus for detecting an electrocardiographic signal, comprising:
a processor; and
a storage medium for storing processor executable instructions,
wherein, the processor is configured to perform the method of claim 5.

12. A machine readable storage medium, wherein the storage medium stores machine executable instructions configured to perform a method of detecting an electrocardiographic signal according to claim 1.

13. An electronic device, comprising:
a processor; and
a storage medium for storing processor executable instructions,
wherein, the processor is configured to perform a method of detecting an electrocardiographic signal according to claim 1.

14. A machine readable storage medium,
wherein the storage medium stores machine executable instructions configured to perform a method of detecting an electrocardiographic signal according to claim 5.

15. An electronic device, comprising:
a processor; and
a storage medium for storing processor executable instructions,
wherein, the processor is configured to perform a method of detecting an electrocardiographic signal according to claim 5.

* * * * *